United States Patent [19]

Tadanier et al.

[11] 4,187,296

[45] Feb. 5, 1980

[54] 2-N-ACYL AND ALKYL 6-EPI-FORTIMICIN B AND DERIVATIVES

[75] Inventors: John S. Tadanier; Jerry R. Martin, both of Waukegan, Ill.

[73] Assignee: Abbott Laboratories, North Chicago, Ill.

[21] Appl. No.: 863,007

[22] Filed: Dec. 21, 1977

[51] Int. Cl.$^2$ .................. A61K 31/71; C07H 15/22
[52] U.S. Cl. ............................ 424/180; 536/4; 536/17 R
[58] Field of Search .............. 424/180; 536/17, 4

[56] References Cited

U.S. PATENT DOCUMENTS

| | | | |
|---|---|---|---|
| 3,931,400 | 1/1976 | Nara et al. | 424/118 |
| 3,976,768 | 8/1976 | Nara et al. | 424/118 |
| 4,060,682 | 11/1977 | Umezawa et al. | 536/17 |

Primary Examiner—Johnnie R. Brown
Attorney, Agent, or Firm—Robert L. Niblack; Gildo E. Fato; Joyce R. Niblack

[57] ABSTRACT

2'-N-Acyl and alkyl-6'-epi-fortimicin B and fortimicin B derivatives represented by the formula

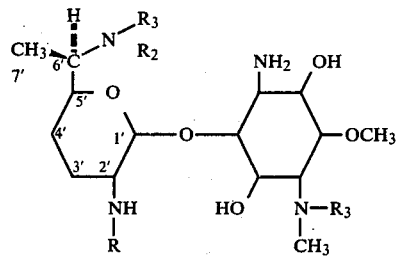

wherein: R is acyl, hydroxyacyl, aminoacyl, N-monoloweralkylamino, N,N-diloweralkylaminoacyl, hydroxy-substituted aminoacyl, an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl or N,N-diloweralkylaminohydroxyloweralkyl; and $R_1$ is acyl, aminoacyl, N-monoloweralkylaminoacyl, N,N-diloweralkylaminoacyl, hydroxy-substituted aminoacyl, an amino acid residue, hydroxyacyl loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, N,N-diloweralkylaminohydroxyloweralkyl or hydrogen; $R_2$ is loweralkyl; and $R_3$ is hydrogen or loweralkyl; and the pharmaceutically acceptable salts thereof; pharmaceutical compositions containing the compounds; and methods of making and using the compounds. The compounds are antibiotics.

10 Claims, No Drawings

2-N-ACYL AND ALKYL 6-EPI-FORTIMICIN B AND DERIVATIVES

BACKGROUND OF THE INVENTION

It is known that the antibacterial and pharmacological properties of many naturally produced aminoglycoside antibiotics can be altered by structural modifications. For example, certain chemical modifications in the gentamicin and kanamycin family of aminoglycoside antibiotics provide compounds which are less toxic than the parent antibiotic. Further, in the same family series mentioned above, certain modifications alter the antibacterial spectrum advantageously either by increasing the intrinsic activity or increasing activity against resistant strains.

Historically, once an aminoglycoside antibiotic has been in clinical use for awhile, resistant microorganisms arise. In many cases, the resistance is R-factor mediated and is attributed to the ability of the bacteria to enzymatically modify the amino or hydroxyl groups of the aminoglycoside antibiotic. Thus there is a continuing need for new fortimicin antibiotic entities.

The present invention provides new and useful fortimicin derivatives.

SUMMARY OF THE DISCLOSURE

2'-N-acyl and alkyl-6'-epi-fortimicin B and derivatives, 4,2'-di-N-acyl and di-N-alkyl-6'-epi-fortimicin B derivatives, 4-N-acyl-2'-N-alkyl-6'-epi and 4-N-alkyl-2'-N-acyl-6'-epi-fortimicin B derivatives are provided by this invention as well as their salts, intermediates, processes for making the compounds, and compositions and methods employing the compounds.

The fortimicin derivatives of this invention are antibiotics which are effective against various Gram-negative and Gram-positive bacteria and can be administered orally or parenterally in daily dosages of from about 1 to about 200 mg/kg of body weight daily to mammalian patients showing symptoms of infection caused by one of the susceptible bacteria.

The compounds can also be used as preservatives for various industrial solutions, in antibacterial scrub solutions for cleaning laboratory bench tops and the like. They are also useful as intermediates in preparing other fortimicin B derivatives which have anti-bacterial activity.

The base fortimicin derivatives of this invention are amines and form salts with fluosilicic acid which are useful as mothproofing agents according to the teachings of U.S. Pat. Nos. 1,915,334 and 2,075,359. They also form salts with thiocyanic acid which condense with formaldehyde to form resinous materials useful as pickling inhibitors as taught in U.S. Pat. Nos. 2,425,320 and 2,606,155.

Derivatives useful in the preparation of the compounds of this invention are provided as well as method of making and using the compounds and compositions employing the compounds.

DETAILED DESCRIPTION OF PREFERRED EMBODIMENTS

The present invention provides 2'-N-acyl and alkyl fortimicin B and derivatives, 4,2'-di-N-acyl and di-N-alkyl derivatives, 4-N-alkyl-2-N acyl and 4-N-acyl-2'-N-alkyl fortimicin B derivatives represented by Formula I:

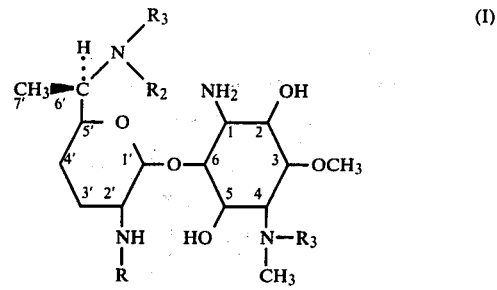

wherein R is acyl, aminoacyl, N-monoloweralkylaminoacyl, hydroxyacyl, N,N-diloweralkylaminoacyl, hydroxy-substituted aminoacyl, an amino acid residue, loweralkyl, aminoloweralkyl, hydroxyloweralkyl, aminohydroxyloweralkyl, N-loweralkylaminoloweralkyl, N,N-diloweralkylaminoloweralkyl, hydroxyloweralkyl, N-loweralkylaminohydroxyloweralkyl or N,N-diloweralkylaminohydroxyloweralkyl and $R_1$ is acyl, aminoacyl, N-monoloweralkylaminoacyl, N,N-diloweralkylaminoacyl, hydroxyacyl hydroxy-substituted aminoacyl, an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, N,N-diloweralkylaminohydroxyloweralkyl, and the pharmaceutically acceptable salts thereof.

The term "pharmaceutically acceptable salts" refers to non-toxic acid addition salts of the compounds of this invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and the like salts.

The term "acyl" refers to groups represented by the formula

wherein $R_1$ is loweralkyl, i.e., acetyl, propionyl, butyryl, etc.

"Lower alkyl" refers to straight or branched chain alkyl radicals having from 1 to 6 carbon atoms, i.e., methyl, ethyl, n-propyl, iso-propyl, n-butyl, sec-butyl, tert-butyl, n-pentyl, 2-methylbutyl, n-hexyl, 2-methylpentyl, 3-methylpentyl, 2,2-dimethylbutyl and the like.

The term "an amino acid residue" refers to D, L or DL-amino acid residues and includes, but is not limited to, glycyl, alanyl, sarcosyl, tyrosyl, phenylalanyl, methionyl, seryl, lysyl, asparaginyl, isoleucyl, leucyl, histidyl, threonyl, aspartyl, asparaginyl, valyl, prolyl, glutaminyl, tryptophanyl, glutamyl and the like.

The 2'-N-acylfortimicin B derivatives of Formula I can be prepared by rearrangement of the corresponding 4-N-substituted fortimicins B of Formula II

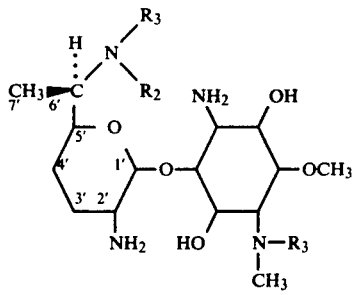

wherein R₂, R₃ and R₄ are as defined in Formula I, or fortimicins A, represented by Formula III

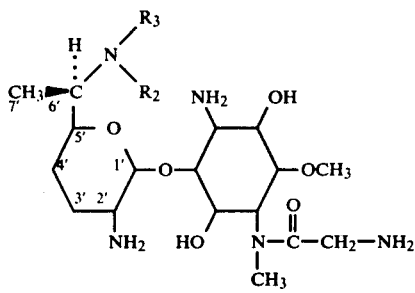

Fortimicin A and fortimicin B are prepared according to the method of U.S. Pat. Nos. 3,976,768 and 3,931,400, respectively. The preparation of representatives 4-N-acyl fortimicin B derivatives is set forth in the examples herein.

Generally speaking, the 6'-epi-intermediates used in preparing the compounds of this invention can be prepared by converting fortimicin B to 1,4,2'-tri-N-acylfortimicin B and thereafter, by reductive amination with, for example, sodium cyanoborohydride and ammonium acetate in methanol, converting the 1,4,2'-tri-N-acyl fortimicin B to 1,4,2'-tri-N-acetyl-6'-epi-fortimicin B which is then converted to the desired material is discussed hereinbelow.

More specifically, fortimicin B is first converted to 1,2'-6'-tri-N-benzyloxycarbonylfortimicin B by, for example, treatment with a suitable acylating agent such as N-benzyloxycarbonyloxysuccinimide. Acetylation of 1,2',6'-tri-N-benzyloxycarbonylfortimicin B results in the corresponding 1,2',6'-tri-N-benzyloxycarbonyl-4-N-acetylfortimicin B. Catalytic hydrogenolysis of the latter in the presence of excess hydrochloric acid in methanol give 4-N-acetylfortimicin B trihydrochloride.

Subsequent treatment of an aqueous solution of the trihydrochloride with at least an equivalent of a suitable anion exchange resin, and then allowing the aqueous solution to stand at ambient temperature for an appropriate interval, gives 2'-N-acetylfortimicin B.

Conversion of 2'-N-acetylfortimicin B to 1,4,2'-tri-N-actylfortimicin B can be accomplished by either of the two following two methods. In the first, 2'-N-acetylfortimicin B is converted to 2'-N-acetyl-6'-N-(5,5-dimethyl-3-oxo-1-cyclohexen-1-yl)-fortimicin B. Di-N-acetylation of the latter gives 1,4,2'-tri-N-acetyl-6'-N-(5,5-diemthyl-3-oxo-1-cyclohexen-1-yl)-fortimicin B. Select removal of the 6'-N-(5,5-dimethyl-3-oxo-1-cyclohexen-1-yl) group gives the desired 1,4,2'-tri-N-acetylfortimicin B.

Alternately, 2'-N-acetylfortimicin B can be converted to 1,6'-di-N-benzyloxycarbonyl-2'-N-acetylfortimicin B, and the latter peracetylated to give 1,6'-di-N-benzyloxycarbonyl-2,5-di-O-acetyl-4,2'-di-N-acetylfortimicin B. Catalytic hydrogenolysis of the above compound in the presence of excess hydrochloric acid in methanol gives 2,5-di-O-acetyl-4,2'-di-N-acetylfortimicin B. Treatment of an aqueous solution of the latter with a suitable anion exchange resin gives the desired 1,4,2'-tri-N-acetylfortimicin B identical with material prepared by the alternate route described above.

Conversion of 1,4,2'-tri-N-acetylfortimicin B to the 6'-N-chloro derivative followed by treatment with a suitable base such as triethylenediamine gives the 6'-imine which is then hydrolyzed to 1,4,2'-tri-N-acetyl-6'-oxo-6'-desaminofortimicin B. Reductive amination of the 6'-oxo-6'-desamino intermediates gives 6'-epi-1,4,2'-tri-N-actylfortimicin B. For example, reductive amination of the 6'-oxo-6'-desamino intermediate with sodium cyanoborohydride and ammonium acetate in methanol gives a mixture of 1,4,2'-tri-N-acetyl-6'-epi-fortimicin B and 1,4,2'-tri-N-acetylfortimicin B in a ratio of about 1:1. Hydrolysis of the latter mixture gives a mixture of 6'-epi-fortimicin B and fortimicin B which is readily converted to a mixture of 1,2',6'-tri-N-benzyloxycarbonyl-6'-epi-fortimicin B and 1,2',6'-tri-N-benzyloxycarbonylfortimicin B. Subsequent reaction with an active ester of 4-N-benzyloxycarbonylglycine, such as the N-hydroxysuccinimide ester, gives a mixture of tetra-N-benzyloxycarbonyl-6'-epi-fortimicin A and tetra-N-benzyloxycarbonylfortimicin A. Catalytic hydrogenolysis of the latter mixture in the presence of excess hydrochloric acid in methanol gives a mixture of 6'-epi-fortimicin A and fortimicin A as the hydrochloride salts, respectively. Alternately, tetra-N-benzyloxycarbonyl-6'-epi-fortimicin A and tetra-N-benzyloxycarbonylfortimicin A may be separated chromotographically. Catalytic hydrogenolysis of pure tetra-N-benzyloxycarbonyl-6'-epi-fortimicin A in the presence of excess hydrochloric acid in methanol gives pure 6'-epi-fortimicin A as the tetrahydrochloride salt.

The mixture of 1,2',6'-tri-N-benzyloxycarbonyl-6'-epi-fortimicin B and 1,2',6'-tri-N-benzyloxycarbonylfortimicin B may be acetylated with a variety of other acyl groups, as defined herein, to give mixtures of 1,2',6'-tri-N-benzyloxycarbonyl-4-N-acyl-6'-epi-fortimicins B and 1,2',6'-tri-N-benzyloxycarbonyl-4-N-acylfortimicin B, from which the 6'-epi-derivatives may be isolated by chromatography. For example, acylation of the mixture of 1,2',6'-tri-N-benzyloxycarbonyl-6'-epi-fortimicin B and 1,2',6'-tri-N-benzyloxycarbonylfortimicin B with the N-hydroxysuccinimide ester of N-benzyloxycarbonylsarcosine gives a mixture of tetra-N-benzyloxycarbonyl-4-N-sarcosyl-6'-epi-fortimicin B and tetra-N-benzyloxycarbonyl-4-N-sarcosylfortimicin B which are separated chromotographically. Acetylation of the mixture of 1,2',6'-tri-N-benzyloxycarbonyl-6'-epi-fortimicin B and 1,2',6'-tri-N-benzyloxycarbonyl fortimicin B with the N-hydroxysuccinimide ester of N-benzyloxycarbonyl-beta-alanine gives a mixture of tetra-N-benzyloxycarbonyl-4-N-beta-alanyl-6-epi-fortimicin B and the tetra-N-benzyloxycarbonyl-4-N-beta-alanylfortimicin B which are separated chromotographically.

Catalytic hydrogenation of the pure 1,2',6'-tri-N-benzyloxycarbonyl-4-N-acetyl-6'-epi-fortimicin B gives the pure 4-N-acyl-6'-epi-fortimicin B which can be conveniently isolated as a perhydrochloride salt. For example, catalytic hydrogenation of tetra-N-benzyloxycarbonyl-4-N-sarcosyl-6'-epi-fortimicin B in the presence of excess hydrochloric acid in methanol gives the pure 4-N-sarcosyl-6'-epi-fortimicin B tetrahydrochloride, while similar treatment of tetra-N-benzyloxycarbonyl-4-N-beta-alanyl-6'-epi-fortimicin B gives the pure 4-N-beta-alanyl-6'-epi-fortimicin B tetrahydrochloride. The corresponding 4-N-alkyl derivatives are conveniently prepared by treating the corresponding per-N-benzyloxycarbonyl-4-N-acyl derivatives with a suitable reducing agent such as diborane. Catalytic hydrogenolysis of the per-N-benzyloxycarbonyl-4-N-alkyl derivatives gives the corresponding 4-N-alkyl fortimicins.

The 2'-N-acetyl, 2'-N-glycyl, and the like 2'-N-acyl or substituted acyl-6'-epi-fortimicins B can readily be prepared by rearrangement of corresponding 4-N-substituted fortimicins. In one method of preparation, the stable acid addition salts of the 4-N-substituted fortimicins are converted to the free bases by, for example, by use of a suitable anion exchange resin. The 2'-N-substituted fortimicins B are then prepared by placing the 4-N-substituted fortimicin free bases in water solution which readily rearranges the $C_4$ carbon substituent to the $C_2$ carbon atom. Treatment of the 2'-N-substituted fortimicins B with suitable N-acylating agents such as N-(benzyloxycarbonyloxy)succinimide, benzyloxycarbonyl chloride or O-(benzyloxycarbonyl) p-nitrophenol in a solvent system such as N,N-dimethylformamide-methanol-water results in the 1,6'-di-N-protected intermediate, i.e., 1,6'-di-N-benzyloxy intermediates, which can be acylated at the 4-N-position with a variety of activated carboxylic acid derivatives, such as a carboxylic acid anhydride, a carboxylic acid chloride, an active carboxylic acid ester, or a carboxylic acid azide.

The active esters may be conveniently prepared by reacting the appropriate carboxylic acid,

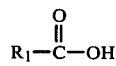

with, for example, 1-hydroxybenzotriazole, N-hydroxysuccinimide, or N-hydroxy-5-norborene-2,3-dicarboximide according to the method of M. Fujino et al., Chem Pharm. Bull, Japan, 22 1857 (1974) wherein $R_1$ is an acyl group as defined in Formula I.

After completion of the N-acylation of the $C_4$-N-methylamino group, it is necessary to remove the benzyloxycarboxyl protecting groups, which can conveniently be carried out by hydrogenolysis over a palladium on carbon catalyst. The fortimicin analogs thus prepared are conveniently osolated as the hydrochloride salts (or other acid addition salts) when the hydrogenolysis is carried out in the presence of a slight excess of hydrochloric acid or another suitable acid.

The 2'-N-alkylfortimicins B are conveniently prepared by treatment of the 2'-N-acylfortimicins B with a suitable reducing agent such as a diborane or a metal hydride such as lithium aluminum hydride. The resulting 2'-N-alkylfortimicins B derivative can then be treated with a suitable N-acylating agent as described above leaving the $C_4$-methylamino group free. $C_4$-N-acylation and deblocking as described previously gives the 4-N-acyl-2'-N-alkylfortimicins B.

The 4,2'-di-N-alkylfortimicins B are conveniently prepared by treating the desired N-protected 4,2'-di-N-actylfortimicin B with a suitable reducing agent, e.g., diborane. Deblocking by hydrogenolysis as described above gives 2'-N-alkyl-4-N-alkylfortimicins B. Alternatively, the 4,2'-di-N-alkylfortimicins can be prepared by reduction of a suitable 4'-N-acyl-2'-N-alkylfortimicin B. For example, a 4-N-acyl-2'-N-alkyl fortimicin B or an N-protected 4-N-acyl-2'-N-alkylfortimicin B may be treated with a suitable reducing agent, e.g., the hydride of diborane. In the case of the resulting N-protected 4,2-di-N-alkylfortimicins B, the N-blocking groups can be conveniently removed by hydrogenolysis providing the 4,2'-di-N-alkylfortimicin B.

Alternatively, the 2'-N-acyl derivatives of this invention can be prepared by reacting fortimicin B with tert-butyl-S-(4,6-dimethyl-pyrimidin-2-yl) thiolcarbonate to obtain the 2'-tert-butyloxycarbonyl (Boc) fortimicin B intermediate.

The 2'-Boc-intermediate is then reacted with a suitable acylating agent, i.e., N-(benzyloxycarbonyloxy)-succinimide which results in the 1,6'-di-N-benzyloxycarbonyl-2'-Boc-fortimicin B intermediate. Treatment of the latter intermediate with an active ester of N-protected glycine, e.g., the hydrosuccinimide ester of N-benzyloxycarbonylglycine in the presence of a suitable solvent system such as N,N-dimethylformamide-methanol-water results in the 2'-Boc-tri-N-benzyloxycarbonylfortimicin B intermediate.

2-N-Alkylation or acylation is then conveniently accomplished by reacting the 2'-deprotected intermediate with a suitable aldehyde ($R_1$CHO) in the presence of sodium borohydride or by treatment with a carboxylic acid ester as described above. Deprotection is then completed by hydrogenolysis in the presence of 5% palladium on carbon catalyst which results in the desired 2'-alkyl or 2'-acyl derivatives.

The following examples further illustrate the invention.

EXAMPLE 1

1,2',6'-Tri-N-benzyloxycarbonylfortimicin B

To a stirred solution of 2.0 g. of fortimicin B, 30 ml. of water and 60 ml. of methanol, cooled in an ice bath, is added 4.44 g. of N-(benzyloxycarbonyloxy)succinimide. Stirring is continued at 0° C. for 3 hours and then at room temperature for 22 hours. The major portion of the methanol is evaporated under reduced pressure and the residue is shaken with a mixture of chloroform and water. The chloroform solution is washed with water and dried over anhydrous magnesium sulfate. The chloroform is evaporated and the residue is chromatographed on silica gel. Elution with a solvent system composed of chloroform-methanol-concentrated ammonium hydroxide (23.4:1.4:0.1 v/v/v) gave 1.05 g of 1,2',6'-tri-N-benzyloxycarbonylfortimicin B:

$[\alpha]_D^{25}$ +16.5° (c 1.0, CH$_3$OH); IR (CDCl$_3$) 1712, 1507 cm$^{-1}$; NMR (CDCl$_3$) δ 1.03 (C$_6$, -CH$_3$, J=6.0 Hz), 2.32 (C$_4$—NCH$_3$), 3.41 (OCH$_3$).

Analysis Calcd. for C$_{39}$H$_{50}$N$_4$O$_{11}$: C, 62.39; H, 6.71; N, 7.46

Found: C, 62.16; H, 6.76; H, 7.43

EXAMPLE 2

1,2',6'-Tri-N-benzyloxycarbonyl-4-N-acetylfortimicin B

To a stirred solution of 3.22 g. of 1,2',6'-tri-N-benzyloxycarbonylfortimicin B, prepared by the method of Example 1, in 225 ml. of methanol, cooled in an ice bath, is added 16 ml. of acetic anhydride over a period of 15 minutes. Stirring is continued at 0° for 2 hours and then at room temperature for 2 hours. The methanol is evaporated under reduced pressure, and residual acetic anhydride and acetic acid are removed by codistillation with benzene and methanol to leave 3.63 g. of 1,2',6'-tri-N-benzyloxycarbonyl-4-N-acetylfortimicin B: $[\alpha]_D^{25}+58.4°$ (c 1.03, $CH_3OH$); NMR ($CDCl_3$) δ 1.16 ($C_6,-CH_3$, J=6.0 Hz), 2.07 ($COCH_3$), 2.83 ($C_4-NCH_3$), 3.34 ($OCH_3$), 4.81 ($H_1$, J=3.0 Hz) IR ($CDCl_3$) 1710, 1620, 1500 $cm^{-1}$.

Analysis Calcd. for $C_{41}H_{52}N_4O_{12}$: C, 62.11; H, 6.61; N, 7.07

Found: C, 62.37; H, 6.74; N, 7.00

EXAMPLE 3

4-N-Acetylfortimicin B trihydrochloride

A solution of 1.03 g. of 1,2',6'-tri-N-benzyloxycarbonyl-4-N-acetylfortimicin B, in 180 ml. of 0.2 N hydrochloric acid in methanol is hydrogenolyzed under 3 atmospheres of hydrogen in the presence of 1.2 g. of 5% palladium on carbon for 4 hours. The catalyst is removed by filtration, and the solvent is evaporated under reduced pressure. Residual water and excess hydrochloric acid are removed by co-distillation with methanol under reduced pressure to yield 0.66 g. of 4-N-acetylfortimicin B trihydrochloride:

$[\alpha]_D^{25}+87.2°$ (c 1.04, $CH_3OH$); IR (KBr) 1600, 1485 $cm^{-1}$; NMR ($D_2O$) δ1.80 ($C_6,-CH_3$, J=6.9 Hz) 2.62 ($COCH_3$), 3.61 ($C_4-NCH_3$), 3.94 ($OCH_3$); 5.77 ($H_1$, J=3.2 Hz);

Mass Spectrum $M^+$. Calcd. 391.2556; Measured 391.2553.

EXAMPLE 4

2'-N-Acetyl-6'-N-(5,5-dimethyl-3-oxo-1-cyclohexen-1-yl)-fortimicin B

An aqueous solution of 2.7 g. of 4-N-acetylfortimicin B trihydrochloride is passed through a column containing an excess of an anion exchange resin, quaternary ammonium styrene type, such as Bio-Rad AG ®2-x8 (OH form) resin sold by Bio-Rad Laboratories, 32nd and Griffin, Richmond, California. The eluate containing the product is diluted to 260 ml. with water, and the resulting solution is allowed to stand at room temperature for four weeks. The water is evaporated under reduced pressure leaving 2.2 g. of crude 2'-N-acetylfortimicin B: IR (KBr) 3350, 1642, 1557 $cm^{-1}$, NMR ($D_2O$) δ 1.50d ($C_6,-CH_3$, J=3.2 Hz), 2.43 ($OCOCH_3$), 2.85 ($C_4-NCH_3$), 3.94 ($OCH_3$).

A magnetically stirred solution of 2.1 g. of the latter, 2.01 g. of 5,5-dimethyl-1,3-cyclohexanedione, and 73 ml. of pyridine is heated in an oil bath at 90° for 23 hours. The pyridine is then evaporated under reduced pressure, and residual pyridine is removed by co-distillation with benzene under reduced pressure. The residue is shaken with a mixture of 200 ml. of chloroform and 200 ml. of water. The chloroform solution is separated and washed twice with 100 ml. portions of water. The aqueous solutions are washed in series with three 100 ml. portions of chloroform. The water solutions are combined and the water is evaporated under reduced pressure. Residual water is removed by co-distillation with methanol under reduced pressure leaving 3.3 g. of crude 2'-N-acetyl-6'-N-(5,5-dimethyl-3-oxo-1-cyclohexen-1-yl)-fortimicin B. The latter product is chromatographed on 200 g. of silica gel, packed as a slurry to a height of 58 cm in a column having an outside diameter (O.D.) of 3.4 cm, with a solvent system composed of chloroform-95% aqueous methanol-concentrated ammonium hydroxide (20.3:4:0.2 v/v/v). Elution is carried out with the solvent system to yield 1.1 g. of pure 2'-N-acetyl-6'-N-(5,5-dimethyl-3-oxo-1-cyclohexen-1-yl)-fortimicin B: $[\alpha]_D^{23}-26.2°$ (c 1.0, $CH_3OH$); IR ($CDCl_3$) 3412, 3300, 1652, 1570, 1540 $cm^{-1}$; NMR ($CDCl_3$) δ 1.06 [$C(CH_3)_2$], 1.92 ($COCH_3$), 2.44 ($C_4-NCH_3$), 3.47 ($OCH_3$); Mass Spectrum Calcd. $(M+H)^+$ 513.3289, Measured 513.3274.

Analysis Calcd. for $C_{25}H_{44}N_4O_7$: C, 58.57; N, 8.65; N, 10.93

Found: C, 58.75; H, 8.70; N, 9.76

EXAMPLE 5

1,4,2'-Tri-N-acetyl-6'-N-(5,5-dimethyl-3-oxo-1-cyclohexen-1-yl)-fortimicin B a. To a magnetically stirred solution of 1.24 g. of pure 2'-N-acetyl-6'-N-(5,5-dimethyl-3-oxo-1-cyclohexen-1-yl)-fortimicin B, cooled in an ice bath, is added 0.6 ml. of acetic anhydride. Stirring is continued at 0° for 3 hours. The chloroform is evaporated under reduced pressure and residual acetic anhydride and acetic acid are removed by co-distillation with methanol under reduced pressure leaving 1.26 g. of 1,4,2'-tri-N-acetyl-6'-N-(5,5-dimethyl-3-oxo-1-cyclohexen-1-yl)-fortimicin B: $[\alpha]_D^{24}+72.1°$ (c 1.0, $CH_3OH$); IR ($CDCl_3$) 3550, 3400, 3325, 1664, 1620, 1570 $cm^{-1}$; NMR ($CDCl_3$) δ 1.04[$C(CH_3)_2$]; 1.20 ($C_6,-CH_3$, J=7 Hz), 1.98, 2.02, 2.12* ($OCOCH_3$), 3.13 ($C_4-NCH$), 3.42 ($OCH_3$); Mass Spectrum $M^+$. Calcd. 596.3422, Measured 596.3439.

*Overlapped by other absorption.

b. To a magnetically stirred solution of 3.9 g. of crude 2'-N-acetyl-6'-N-(5,5-dimethyl-3-oxo-1-cyclohexen-1-yl)-fortimicin B in 385 ml. of chloroform, cooled in an ice bath, is added 2.0 ml. of acetic anhydride. Stirring is continued at 0° for 4 hours. The chloroform is evaporated under reduced pressure. Residual acetic acid and acetic anhydride are removed by co-distillation with methanol to leave 4.8 g. of orange glass. A sample of 2.4 g. of the product is chromatographed on 200 g. of silica gel packed as a slurry in a 3.4 cm O.D. column to a height of 59 cm with a solvent system composed of chloroform-95% aqueous methanol-concentrated ammonium hydroxide (21.3:3:0.2 v/v/v) to yield 1.0 g. of pure 1,4,2'-tri-N-actyl-6'-N-(5,5-dimethyl-3-oxo-1-cyclohexen-1-yl)-fortimicin B identical in all respects with the material prepared as described in part a.

EXAMPLE 6

1,6'-Dibenzyloxycarbonyl-2'-N-acetylfortimicin B

To a magnetically stirred solution of 3.2 g. of crude 2'-N-acetylfortimicin B, 45 ml. of water, and 90 ml. of methanol, cooled in an ice bath, is added 4.3 g. of N-(benzyloxycarbonyloxy)succinimide. Stirring is continued at 0° for 3 hours and then at ambient temperature for 20 hours. The major portion of the methanol is evaporated under reduced pressure, and the residue is shaken with a mixture of 400 ml. of 5% aqueous sodium bicarbonate and 300 ml. of chloroform. The chloroform solution is separated and washed with 400 ml. of saturated aqueous sodium chloride solution. The aqueous solutions are washed in series with four 100 ml. portions of chloroform. The chloroform solutions are combined and dried over anhydrous magnesium sulfate. Evaporation of the chloroform under reduced pressure leaves 4.2 g. of white glass. The latter product is chromatographed on 250 g. of silica gel packed as a slurry in a 3.4 cm O.D. column to a height of 75 cm, in a solvent system composed of chloroform-methanol-concentrated ammonium hydroxide (23.3:1.4:0.1 v/v/v). After eluting with 1.7 liters of the above solvent system, elution was carried out with a solvent system composed of chloroform-methanol-concentrated ammonium hydroxide (20.8:4:0.1 v/v/v) to yield 1.4 g. of 1,6'-dibenzyloxycarbonyl-2'-N-acetylfortimicin B: IR (CDCl$_3$) 3550, 3440, 3338, 1708, 1658 cm$^{-1}$; NMR (CDCl$_3$) δ 0.99 (C$_6$'—CH$_3$, J=6 Hz), 1.32 (OCOCH$_3$), 2.43 (C$_4$NCH$_3$), 3.46 (OCH$_3$), 4.93 (C$_1$,—H, unresolved).
Elemental analysis was in agreement with the structure.

EXAMPLE 17

1,6'-Di-N-benzyloxycarbonyl-2,5-di-O-acetyl-4,2'-di-N-acetylfortimicin B

To a magnetically stirred solution of 1.00 g. of 1,6'-di-N-benzyloxycarbonyl-2'-N-acetylfortimicin B in 9 ml. of pyridine is added 3 ml. of acetic anhydride. Stirring is continued at room temperature for 24 hours. The resulting solution is poured cautiously into a solution of 15 g. of sodium bicarbonate in 200 ml. of water. Excess solid sodium bicarbonate is added, and the resulting suspension is extracted with 200 ml. of chloroform. The chloroform solution is separated and washed with 200 ml. of water. The aqueous solutions are washed in series with three 100-ml. portions of chloroform and the chloroform solutions are combined. The chloroform is evaporated under reduced pressure and residual pyridine is removed by co-distillation with benzene under reduced pressure leaving 1.2 g. of 1,6'-di-N-benzyloxycarbonyl-2,5-di-O-acetyl-4,2'-di-N-acetyl B: IR (CHCl$_3$): 3452, 3370, 1745, 1714, 1660, 1632 cm$^{-1}$ NMR (CDCl$_3$) δ 1.24 (C$_6$'—CH$_3$, unresolved), 3.37 (OCH$_3$), 479 (H$_1$', J=3.2 Hz).
Elemental analysis was in agreement with the structure.

EXAMPLE 8

2,5-Di-O-acetyl-4,2'-di-N-acetylfortimicin B trihydrochloride

A sample of 1,6'-di-N-benzyloxycarbonyl-2,5-di-O-acetyl-4,2'-di-N-acetylfortimicin B in a solution with 60 ml. of 0.2 N hydrochloric acid in methanol and 40 ml. of methanol is catalytically hydrogenated under three atmospheres of hydrogen for three hours in the presence of 1.2 g. of 5% palladium on carbon. The catalyst is removed by filtration, and the methanol is evaporated under reduced pressure. Residual water is removed by co-distillation with methanol leaving 0.90 g. of 2,5-di-O-acetyl-4,2'-di-N-acetylfortimicin B trihydrochloride: IR (KBr) 1746, 1620 cm$^{-1}$; NMR (D$_2$O) δ 1.75 (C$_6$'—CH$_3$, J=6.6 Hz) 2.46 (3H), 2.60 (3H), 2.66 (6H), (COCH$_3$); 3.48 (C$_4$—NCH$_3$), 3.92 (OCH$_3$).

EXAMPLE 9

1,4,2'-Tri-N-acetylfortimicin B a. To a magnetically stirred mixture of 2.1 g. of 1,4,2'-tri-N-acetyl-6'-N-(5,5-dimethyl-3-oxo-1-cyclohexen-1-yl)-fortimicin B, 50 ml. of chloroform, and 200 ml. of water, cooled in an ice bath is added, in a period of 4 minutes, a freshly prepared solution of 3 g. of chlorine in 50 ml. of carbon tetrachloride. Stirring is continued for 5 minutes. and then there is added 34 ml. of 5% aqueous sodium bisulfite, followed after a minute by 14 ml. of dilute ammonium hydroxide. The mixture is transferred to a 1 liter separatory funnel and the organic phase and the aqueous phase are diluted to 340 ml. with chloroform and water, respectively. The chloroform solution is separated and extracted with 300 ml. of water. The aqueous solutions are washed in series with two 180 ml. portions of chloroform and then combined. Ethanol (200 ml.) is added to the aqueous solution as an antifoam, and the solvent is evaporated under reduced pressure. The residue is triturated six times with 80 ml. portions of methanol, and the supernatant is filtered through a sintered glass funnel. The methanol is evaporated under reduced pressure, and the residue is triturated five times with 50 ml. portions of a solvent system prepared from the lower phase of a mixture of chloroform-methanol-concentrated ammonium hydroxide-water (2:2:1:1 v/v/v/v). The supernatant is filtered, and the solvent evaporated from the filtrate under reduced pressure leaving 1.0 g. of a light yellow glass. The latter product was chromatographed on 220 g. of silica gel packed as a slurry in a 3.4 cm. O.D. column to a height of 65 cm with a solvent system prepared from the lower phase of a mixture of chloroform-methanol-concentrated ammonium hydroxide-water (2:2:1:1 v/v/v/v). Elution is carried out with the solvent system to yield 1.0 g. of 1,4,2'-tri-N-acetylfortimicin B: [α]$_D^{23}$+112° (c 1.0, CH$_3$OH); IR (CDCl$_3$) 1620, 1610 cm$^{-1}$; NMR (CDCl$_3$) δ 1.08 (C$_6$'—CH$_3$, J=6 Hz) 1.98 (6H), 2.15 (3H), (OCOCH$_3$), 3.15 (C$_4$—NCH$_3$), 3.41 (OCH), 4.82 (C$_1$'—H, J=4 Hz); Mass Spectrum: M+. Calcd. 474.2690 Measured: 474,2694 b. 1,4,2'-tri-N-acetylfortimicin B is also prepared from 2,5-di-O-acetyl-4,2'-di-N-acetylfortimicin B trihydrochloride by the following procedure. An aqueous solution of 0.86 g. of 2,5-di-O-acetyl-4,2'-di-N-acetylfortimicin B trihydrochloride is passed through an 0.8 cm O.D. column packed to a height of 20 cm with 10 ml. of a anion exchange resin quaternary ammonium styrene type such as Bio-Rad AG ® 2-X8(OH form) resin (50–100 mesh) sold by Bio-Rad Laboratories, 32nd and Griffin, Richmond, Calif. To the eluate (50 ml.) containing the product is added 50 ml. of ethanol as an antifoam. The solvent is evaporated under reduced pressure. Residual water is removed by co-distillation with methanol leaving 0.64 g. of 1,4,2'-tri-N-acetylfortimicin B which is identical in all respects with that prepared by the procedure described above in part a.

EXAMPLE 10

1,4,2'-Tri-N-acetyl-6'-imino-6'-desaminofortimicin B and 1,4,2'-Tri-N-acetyl-6'-oxo-6'-desaminofortimicin B To a magnetically stirred solution of 1,4,2'-tri-N-acetylfortimicin B in 5 ml. of methylene chloride is added 0.040 g. of N-chlorosuccinimide and 1 ml. of methylene chloride. Stirring is continued for 40 minutes. The methylene chloride is evaporated under reduced pressure leaving crude 1,4,2'-tri-N-acetyl-6'-N-chlorofortimicin B as a white glass. The latter product is heated under reflux for 1 hour in a solution prepared from 10 ml. of 1% triethylenediamine in ethanol. The ethanol is evaporated under reduced pressure and the residue is chromatographed on 20 g. of silica gel packed as a slurry in a 1.8 cm O.D. column to a height of 22 cm with a solvent system composed of methylene chloride-95% aqueous methanol (20.3:4 v/v). Five-milliter fractions are collected. Fractions 8–11 are combined and solvent is evaporated to yield 46 mg. of white glass. To remove succinimide the latter material, in methanol solution, is passed through a column of an excess of an anion exchange resin, quarternary ammonium styrene type, such as Bio-Rad AG ® 2-X8 (OH form), packed in methanol. Evaporation of the methanol from the eluate leaves 39 mg. of 1,4,2'-tri-N-acetyl-6'-imino-6'-desaminofortimicin B: IR (CDCl$_3$) 1660, 1620 cm$^{-1}$; NMR (CDCl$_3$) δ 1.98, 2.00, 2.13 (OCOCH$_3$), 2.19 (C$_6$'—CH$_3$), 4.84 (C$_1$'—H, J=3.3 Hz).

Further eluation of the silica gel column gives 28 mg. of 1,4,2'-tri-N-acetyl-6'-oxo-6'-desaminofortimicin B identical with that described in Example 12.

EXAMPLE 11

1,4,2'-Tri-N-acetyl-6'-imino-6'-desaminofortimicin B

To a magnetically stirred solution of 307 mg. of 1,4,2'-tri-N-acetylfortimicin B in 15 ml. of methylene chloride at 0° is added 94 mg. of N-chlorosuccinimide. Stirring is continued at 0° for 0.5 hours. The methylene chloride is evaporated under reduced pressure leaving the crude 1,4,2'-tri-N-acetyl-6'-N-chlorofortimicin B as a white glass. The latter product is kept for 24 hours at room temperature in 30 ml. of a 1% solution of triethylenediamine in ethanol which has been previously dried overnight over 3A molecular sieve. Thin layer chromatography on an aliquot of the reaction solution (methylene chloride-95% aqueous methanol) shows that the corresponding 6'-imine is virtually the exclusive product. The solvent is evaporated under reduced pressure and the residue is chromatographed on 35 g. of silica gel packed as a slurry in a 1.8 cm O.D. column to a height of 38 cm in a solvent system composed of methylene chloride-95% aqueous methanol (20.3:4 v/v). Elution with the solvent system gives 128 mg. of product. To remove succinimide the latter is dissolved in methanol and passed through a column of an excess of an anion exchange resin, quaternary ammonium styrene type such as Bio-Rad AG$^R$ 2-X8 (OH form) (50–100 mesh). Evaporation of the methanol from the eluate containing the product gives 116 mg. of 1,4,2'-tri-N-acetyl-6'-imino-6'-desaminofortimicin B identical in all respects with the product described in Example 10.

EXAMPLE 12

1,4,2'-Tri-N-acetyl-6'-oxo-6'-desaminofortimicin B

To a magnetically stirred solution of 1.48 g. of 1,4,2'-tri-N-acetylfortimicin B in 72 ml, of methylene chloride, cooled to 0° in an ice bath, is added 0.64 g. of N-chlorosuccinimide. Stirring is continued at 0° for 45 minutes, and the solvent is then evaporated under reduced pressure to leave the crude 1,4,2'-tri-N-acetyl-6'-N-chlorofortimicin B as a white glass. The latter product is heated under reflux for 1 hour in 142 ml. of a solution of 1% triethylenediamine in ethanol. Thin layer chromatography on an aliquot of the resulting solution (methylene chloride-95% aqueous methanol, 20.3:4 v/v) shows the pressure of 1,4,2'-tri-N-acetyl-6'-imino 6'-aminofortimicin B and 1,4,2'-tri-N-acetyl-6'-oxo-6'-desaminofortimicin B in the ratio of about 1:1. The solvent is evaporated under reduced pressure and the residue chromatographed in 80 g. of silica gel packed with a solvent system composed of methylene chloride-95% aqueous methanol (20.3:4 v/v). Early fractions contained the pure 6'-amino and later fractions contained the pure 6'-ketone. All fractions are combined and solvent is evaporated under reduced pressure to leave 1.62 g. of a mixture of the pure 6'-imino and the pure 6'-ketone. The latter mixture is dissolved in 74 ml. of 0.2 N-hydrochloric acid and the resulting solution is kept at room temperature for 0.5 hours and then passed through a column of excess anion exchange resin, quaternary ammonium styrene type, such as Bio-Rad AG ® 2-X8 (OH form), 50–100 mesh. Evaporation of water from the eluate containing the product gives 0.94 g. of 1,4,2'-tri-N-acetyl-6'-oxo-6'-desaminofortimicin B: $[\alpha]_D^{23}$+99.7° (c 1.0, CH$_3$OH); IR (CDCl$_3$) 1720, 1660, 1620 cm$^{-1}$; NMR (CDCl$_3$) δ 1.97, 1.98, 2.14 (OCOCH$_3$) 2.22 (C$_6$'—CH$_3$), 3.14 (C$_4$—NCH$_3$), 3.41 (OCH$_3$), 4.84 (H$_1$', J=3.3 Hz). Mass Spectrum: M$^+$. Calcd. 473.2373, Measured 473.2371.

EXAMPLE 13

1,4,2'-Tri-N-acetyl-6'-epi-fortimicin B and 1,4,2'-Tri-N-acetylfortimicin B a. A magnetically stirred solution of 1,4,2'-tri-N-acetyl-6'-oxo-6'-desaminofortimicin B, 3.01 g. of ammonium acetate, 0.304 g. of sodium cyanoborohydride, and 40 ml. of methanol is kept at room temperature for 22 hours. The solvent is evaporated under reduced pressure and the residue is chromatographed on 160 g. of silica gel using a solvent system prepared from the lower phase of a mixture composed of chloroform-methanol-concentrated ammonium hydroxide-water (3:3:1:2 v/v/v/v) to yield 0.61 g. of a mixture of about 1:1 1,4,2'-tri-N-acetyl-6'-epi-fortimicin B and 1,4,2'-tri-N-acetylfortimicin B: NMR (CDCl$_3$) δ 1.06 (C$_6$'—CH$_3$, J=6.7 Hz), individual peaks of doublet significantly broadened), 1.98 (6H), 2.14 (3H) (OCOCH$_3$), 3.14 (C$_4$—NCH$_3$), 3.39 (OCH$_3$), 4.80 (C$_1$'—H, J=3 Hz); Mass Spectrum, M$^+$., Calcd. 474.2690, Measured 474.2675.

b. A magnetically stirred solution of 1.32 g. of a mixture of about 1:1 1,4,2'-tri-N-acetyl-6'-imino-6'-desaminofortimicin B and 1,4,2'-tri-N-acetyl-6'-oxo-6'-desaminofortimicin B, 2.57 g. of ammonium acetate, 0.255 g. of sodium cyanoborohydride, and 35 ml. of methanol is stirred at room temperature for 22 hours. The solvent is evaporated and the residue is chromatographed on 150 g. of silica gel using a solvent system prepared from the lower phase of a mixture of chloroform-methanol-concentrated ammonium hydroxide-water (3:3:1:2 v/v/v/v). The earlier fractions yield 0.61 g. of a mixture of 1,4,2'-tri-N-acetyl-6'-epi-fortimicin B and 1,4,2'-tri-N-acetylfortimicin B in a ratio of about 1:1. The latter fractions yield 0.35 g. of 1,4,2'-tri-N-acetyl-6'-imino-6'-desaminofortimicin B.

Treatment of 0.30 g. of latter product, thus obtained, with 0.2 N hydrochloric acid followed by excess anion exchange resin, quaternary ammonium sytrene type such as Bio-Rad AG ® 2-X8 (OH form) gives 0.25 g. of 1,4,2'-tri-N-acetyl-6'-oxo-6'-desaminofortimicin B. Reductive amination of 0.24 g. of the latter with sodium borohydride and ammonium acetate in methanol yields 0.21 g. of a mixture of 1,4,2'-tri-N-acetyl-6'-epi-fortimicin B and 1,4,2'-tri-N-acetylfortimicin B in a ratio of about 1:1, identical with that described above.

EXAMPLE 14

6'-epi-Fortimicin B and Fortimicin B

A solution prepared from a mixture (0.99 g.) of about 1:1 1,4,2'-tri-N-acetyl-6'-epi-fortimicin B and 1,4,2'-tri-N-acetylfortimicin B, prepared as described in Example 10, and 10 ml. of 4 M sodium hydroxide is kept at 100° for 18 hours. Water (20 ml.) is added and sufficient 4 M hydrochloric acid is slowly added to the cooled solution to bring the pH to seven. The water is evaporated under reduced pressure and the residue is triturated with six, 50 milliliter portions of methanol. The methanol supernatant is filtered through a sintered glass funnel and the methanol is evaporated from the filtrate under reduced pressure. The residue is chromatographed on 80 g. of silica gel using a solvent system prepared from the lower phase of a mixture of chloroform-methanol-concentrated ammonium hydroxide (1:1:1 v/v/v), to yield 0.55 g. of a mixture of 6'-epi-fortimicin B and fortimicin B in a ratio of about 1:1: $[\alpha]_D^{20} + 30°$ (c 1.0, CH$_3$OH), NMR (D$_2$O) δ 0.99 (C$_{6'}$—CH$_3$, J=6 Hz), 1.02 (C$_{6'}$—CH$_3$, J=6.5 Hz) 2.84 (C$_4$—NCH$_3$). 3.92 (OCH$_3$), 5.48 (H$_{1'}$, J=3.5 Hz), 5.51 (H$_{1'}$, J=3.5 Hz); Mass Spectrum: M$^+$. Calcd. 348.2373, Found 348.2368.

EXAMPLE 15

1,2,6'-Tri-N-benzyloxycarbonyl-6'-epi-fortimicin B and 1,2,6'-Tri-N-benzyloxycarbonylfortimicin B To a magnetically stirred solution of 0.701 g. of a mixture of 6'-epi-fortimicin B and fortimicin B in a ratio of about 1:1, prepared as described in Example 1 cooled to 0°, 20 ml. of methanol and 10 ml. of water, is added 1.57 g. of N-benzyloxycarbonyloxysuccinimide. Stirring is continued at 0° for 3 hours and then at ambient temperature for 20 hours. The resulting solution is shaken with a mixture of 250 ml. of chloroform and 250 ml. of water. The chloroform solution is separated and washed with 250 ml. of water. The aqueous solutions are washed in series with three 100-ml. portions of chloroform. The chloroform solutions are combined and the chloroform is evaporated under reduced pressure leaving 1.48 g. of a mixture of 1,2',6'-tri-N-benzyloxycarbonyl-6'-epi-fortimicin B and 1,2',6'-tri-N-benzyloxycarbonylfortimicin B in a ratio of about 1:1, as a white glass: $[\alpha]_D^{22} + 18°$ (c 1.0, CH$_3$OH), NMR (CDCl$_3$) δ 1.00 d (C$_{6'}$—CH$_3$, J=6 Hz), 2.32 (C$_4$—NCH$_3$), 3.40 (OCH$_3$), Elemental analysis is in agreement with the empirical formula C$_{39}$H$_{50}$N$_4$O$_{11}$.

EXAMPLE 16

Tetra-N-benzyloxycarbonyl-6'-epi-fortimicin A

To a magnetically stirred solution of 0.784 g. of a mixture of 1,2',6'-tri-N-benzyloxycarbonyl-6'-epi-fortimicin B and 1,2',6'-tri-N-benzyloxycarbonylfortimicin B in a ratio of about 1:1, prepared as described in Example 15, in 8 ml. of tetrahydrofuran, cooled to 0°, is added 0.357 g. the N-hydroxysuccinimide ester of N-benzyloxycarbonylglycine Stirring is continued at 0° for 4.5 hours and then at ambient temperature for 22 hours. The resulting solution is shaken with a mixture of 200 ml. of chloroform and 200 ml. of 5% aqueous sodium bicarbonate. The chloroform solution is separated and washed with 200 ml. of water. The aqueous solutions are washed in series with four 100-ml. portions of chloroform. The chloroform solutions are combined, and the chloroform is evaporated under reduced pressure to yield 1.03 g. of white glass. The latter product is chromatographed on 70 g. of silica gel packed as a slurry in a 2.4 cm O.D. column to a height of 42 cm with a solvent system composed of benzene-methanol-ethanol-concentrated ammonium hydroxide (23.5:16:1.80:0.2 v/v/v/v). Elution is carried out with the solvent system to yield 0.91 g. of a mixture of tetra-N-benzyloxycarbonyl-6'-epi-fortimicin A and tetra-N-benzyloxycarbonylfortimicin A in a ratio of about 1:1: $[\alpha]_D^{22} + 58°$ (c 1.0, CH$_3$OH); IR (CDCl$_3$) 3570, 3430, 1705, 1630 cm$^{-1}$; NMR (CDCl$_3$) δ 1.0–1.3 (C$_{6'}$—CH$_3$ unresolved multiplet), 2.80 (C$_4$—NCH$_3$), 3.26, 3.29 (OCH$_3$).

Analysis Calcd. for C$_{49}$H$_{59}$N$_5$O$_{14}$: C, 62.48; H, 6.31; N, 7.43

Found: C, 62.20; H, 6.24; N, 7.31

A sample of 0.788 g. of a mixture of tetra-N-benzyloxycarbonyl-6'-epi-fortimicin A and tetra-N-benzyloxycarbonylfortimicin A (~1:1 ratio) is chromatographed on 75 g. of silica gel packed as a slurry in a 2.4 O.D. cm column to a height of 46 cm with ethyl acetate. Elution is carried out with ethyl acetate and five-milliliter fractions are collected. Fractions 34–37 contain 0.138 g. of pure tetrabenzyloxycarbonyl-6'-epi-fortimicin A isolated as a white glass after evaporation of the ethyl acetate under reduced pressure: $[\alpha]_D^{22} + 69°$ (c 1.0, CH$_3$OH); IR (CDCl$_3$) 3540, 3420, 1700, 1630 cm$^{-1}$; NMR (CDCl$_3$) δ 1.12 (C$_{6'}$—CH$_3$, J=6 Hz), 2.82 (C$_4$—NCH$_3$), 3.26 (OCH$_3$), 4.86 (C$_1$,—H unresolved multiplet, W1/2 J=7 Hz).

Analysis Calcd. for C$_{49}$H$_{59}$N$_5$O$_{14}$: C, 62.48; H, 6.31; N, 7.43

Found: C, 62.00; H, 6.41; N, 7.00

Fractions 38–46 are combined, and evaporation of solvent leaves a mixture of tetra-N-benzyloxycarbonyl-6'-epi-fortimicin A and tetra-N-benzyloxycarbonylfortimicin A in a ratio of about 1:1 as a white glass. Rechromatography of the latter mixture on silica gel with ethyl acetate gives additional pure tetra-N-benzyloxycarbonyl-6'-epi-fortimicin A.

Further elution of the original silica gel column with ethyl acetate gives pure tetra-N-benzyloxycarbonylfortimicin A in fractions 47–77. Evaporation of the ethyl acetate under reduced pressure gives an additional 0.17 g. of pure tetra-N-benzyloxycarbonylfortimicin A.

EXAMPLE 17

Tetra-N-benzyloxycarbonyl-4-N-sarcosyl-6'-epi-fortimicin B

To a magnetically stirred solution of 0.83 g. of a mixture of 1,2',6'-tri-N-benzyloxycarbonyl-6'-epi-fortimicin B and 1,2',6'-tri-N-benzyloxycarbonylfortimicin B(~1:1 ratio), prepared as described in Example 15, in 9 ml. of tetrahydrofuran, cooled to 0°, is added 0.448 g. of the N-hydroxysuccinimide ester of N-benzyloxycarbonylsarcosine. Stirring is continued at 0° for 3 hours, and then at ambient temperature for 22 hours. The product is isolated as a white glass by chloroform extraction as described in Example 13. Chromatography of the latter product on silica gel gives pure tetra-N-benzyloxycarbonyl-4-N-sarcosyl-6'-epi-fortimicin B. NMR, IR, and mass spectra are compatible with the structure.

EXAMPLE 18

Tetra-N-benzyloxycarbonyl-4-N-β-alanyl 6'-epi-fortimicin B

To a magnetically stirred solution of 0.87 g. of a mixture of 1,2',6'-tri-N-benzyloxycarbonyl-6'-epi-fortimicin B and 1,2',6'-tri-N-benzyloxycarbonylfortimicin B(~1:1 ratio) prepared as described in Example 15, in 9 ml. of tetrahydrofuran, cooled to 0°, is added to 0.452 g. of the N-hydroxysuccinimide ester of N-benzyloxycarbonyl-β-alanine. Stirring is continued at 0° for 3 hours, and then at ambient temperature for 24 hours. The product is isolated as a white glass by chloroform extraction as described in Example 13. Chromatography of the latter product on silica gel gives pure tetra-N- benzyloxycarbonyl-4-N-beta-alanyl-6'-epi-fortimicin B. NMR, IR, and mass spectra are compatible with the structure.

EXAMPLE 19

6'-epi-Fortimicin A Tetrahydrochloride and Fortimicin A Tetrachloride

A sample of 0.40 g. of a 1:1 mixture of tetra-N-benzyloxycarbonyl-6'-epi-fortimicin A and tetra-N-benzyloxycarbonylfortimicin A, prepared as described in Example 16, in 35 ml. of 0.2 N-hydrochloric acid in methanol in the presence of 0.4 g. of 5% palladium on carbon, is hydrogenated under 3 atmospheres of hydrogen for 4 hours at room temperature. The catalyst is removed by filtration and the solvent is evaporated under reduced pressure. Residual water is removed by co-distillation with methanol under reduced pressure to leave 0.233 g. of a mixture of 6'-epi-fortimicin A tetrahydrochloride and fortimicin A tetrahydrochloride (~1:1 ratio) as a powder: $[\alpha]_D^{21} +76°$ (c 1.0, $CH_3OH$), IR (KBr) 1640 $cm^{-1}$; NMR ($D_2O$) δ 1.76 ($C_6$—$CH_3$, J=7 Hz), 1.80 ($C_6'$—$CH_3$, J=7 Hz), 3.58 ($C_4$—$NCH_3$), 3.94 ($OCH_3$), 5.78 ($H_1$, J=3.6 Hz). Mass Spectrum $M^+$. Calcd. 405.2578, Measured 405.2557.

EXAMPLE 20

6'-epi-Fortimicin A Tetrahydrochloride

A sample of 0.4883 g. of tetra-N-benzyloxycarbonyl-6'-fortimicin A in 52 ml. of 0.2 N-hydrochloric acid in methanol in the presence of 0.48 g. of 5% palladium on carbon is hydrogenated under 3 atmospheres of hydrogen for 4 hours at room temperature. The catalyst is removed by filtration and the solvent is evaporated under reduced pressure. Residual water is removed by co-distillation with methanol under reduced pressure to leave 0.270 g. of 6'-fortimicin A tetrahydrochloride as a white powder: $[\alpha]_D^{22} +89°$ (c 1.0, $CH_3OH$), IR (KBr): 1650 $cm^{-1}$; NMR ($D_2O$) δ 1.77 ($C_6'$—$CH_3$, J=7 Hz), 3.59 ($C_4$—$NCH_3$), 3.95 ($OCH_3$), 5.78 ($H_{1'}$,J=3.6 Hz).

EXAMPLE 21

4-N-Sarcosyl-6'-epi-Fortimicin B Tetrahydrochloride

A sample of tetra-N-benzyloxycarbonyl-4-N-sarcosyl-6'-epi-fortimicin B, prepared as described in Example 17, is catalytically hydrogenated by the procedure of Example 20 to give 4-N-sarcosyl-6'-epi-fortimicin B tetrahydrochloride.

EXAMPLE 22

4-N-β-Alanyl-6'-epi-Fortimicin B Tetrachloride

A sample of tetra-N-benzyloxycarbonyl-4-N-beta-alanyl-6'-epi-fortimicin B, prepared as described in Example 18, is catalytically hydrogenated by the procedure of Example 20 to give 4-N-beta-alanyl-6'-epi-fortimicin B tetrahydrochloride.

EXAMPLE 23

2'-N-Glycyl-6'-epi-fortimicin B

An aqueous solution of 10.0 g. of 6'-epi-fortimicin A disulfate (1) is passed through a column of an anion exchange resin, quaternary ammonium styrene type, e.g., Bio-Rad Laboratories, AG ® 2-X8 resin, 100–200 mesh, hydroxyl form, sufficient to remove the sulfate ion. The basic elutes are collected and dilute with water to a 1% solution based on starting fortimicin A disulfate. After standing at 37° C. for 20 days the water is evaporated under reduced pressure to leave an oil. A 2.07 g portion of the oil is chromatographed on a column (2.2×52 cm) of a cation exchange resin, carboxylic type, e.g., Bio-Rad Laboratories, Bio-Rex 70, (100–200 mesh, ammonium form) and eluted with 0.1 N ammonium hydroxide. Elutes containing only 2'-N-glycyl-6'-epi-fortimicin B are collected, evaporated to a small volumne under reduced pressure and lyophilized to give the desired product.

EXAMPLE 24

2'-N-(N-Benzyloxycarbonylglycyl)-1,6'-di-N-benzyloxycarbonyl-6'-epi-fortimicin B A stirred solution of 0.333 g. of 2'-N-glycyl-6'-fortimicin B in 4.5 ml of water and 9.0 ml of methanol cooled to 4° C. in an ice bath, is treated with 0.666 g of N-(benzyloxycarbonyloxy)succinimide. Stirring is continued at 4° C. for 3 hours and then at room temperature for 20 hours. The resulting solution is concentrated under reduced pressure to an oil. The oil is shaken with a mixture of 150 ml of chloroform and 75 ml of water. The chloroform layer is separated and washed with 75 ml of water. The aqueous portions are washed in series with two 75 ml portions of chloroform. The chloroform solutions are combined and dried over anhydrous magnesium sulfate. Evaporation of the chloroform under reduced pressure leaves 0.596 g of product. The product is chromatographed on a column (1.8×48 cm) of silica gel prepared and eluted with a solvent system consisting of chloroform methanol-ammonium hydroxide (23.4: 1.4:0.1 v/v) to yield the desired product.

EXAMPLE 25

Tetra-N-benzyloxycarbonyl-2'-N-glycyl-6'-epi-fortimicin A

To a stirred solution of 0.234 g. of 2'-N-(N-benzyloxycarbonylglycyl)-1,6'-di-N-benzyloxycarbonyl-6-epi-fortimicin B 0.105 g. of N-benzyloxycarbonylglycine and 0.939 g. of 1-hydroxybenzotriazole monohydrate in 2.0 ml tetrahydrofuran is added 0.087 g. of N,N-dicyclohexylcarbodiimide in 2.0 ml of tetrahydrofuran. Stirring is continued for 20 hours at room temperature. Insoluble dicyclohexylurea is removed by filtration and the filtrate is concentrated to dryness under reduced pressure to give 0.408 g of a solid. The solid is chromatographed on a column (1.8×42 cm) of silica gel eluted with a solvent system consisting of benzene-methanol-95% ethanol-ammonium hydroxide (23.5:1.4:2.0:0.2 v/v/v/v) to give the desired product.

EXAMPLE 26

2'-N-Glycyl-6'-epi-fortimicin A tetrahydrochloride

A solution of 0.235 g. of tetra-N-benzyloxycarbonyl-2'-N-glycyl-6'epi-fortimicin A in 40 ml. of 0.2 N hydrochloric acid in methanol is hydrogenolyzed for 4 hours under 3 atmospheres of hydrogen in the presence of 0.235 g of 5% palladium on carbon. The catalyst is removed by filtration through a celite mat. The filtrate is concentrated to dryness and excess hydrochloric acid is removed by repeated co-distillation with methanol under reduced pressure to give the desired product.

EXAMPLE 27

1,2',6'-Tri-N-benzyloxycarbonylfortimicin B

To a stirred solution of 2.0 g. of 6'-epi-fortimicin B 30 ml of water and 60 ml of methanol, cooled in an ice bath, is added 4.44 g of N-(benzyloxycarbonyloxy)succinimide. Stirring is continued at 0° for 3 hours and then at room temperature for 22 hours. The major portion of the methanol is evaporated under reduced pressure and the residue is shaken with a mixture of chloroform and water. The chloroform solution is washed with water and dried over anhydrous magnesium sulfate. The chloroform is evaporated and the residue is chromotographed on silica gel. Elution with a solvent system composed of chloroform-methanol-concentrated ammonium hydroxide (23.4:1.4:0.1 v/v/v) gives the desired product.

EXAMPLE 28

1,2',6'-Tri-N-benzyloxycarbonyl-4-N-acetyl-6'-epi-fortimicin B

To a stirred solution of 3.22 g. of 1,2',6'-tribenzyloxycarbonyl-6'-epi-fortimicin B in 225 ml of methanol, cooled, in an ice bath, is added 16 ml of acetic anhydride over a 15 minute period. Stirring is continued at 0° for 2 hours and then at room temperature for 2 hours. The methanol is evaporated under reduced pressure and residual acetic anhydride and acetic acid are removed by co-distillation with benzene and methanol to leave the desired product.

EXAMPLE 29

4-N-Acetyl-6'-epi-fortimicin B trihydrochloride

A solution of 1.0274 g. of tri-N-benzyloxycarbonyl-4-N-acetyl-6'-epi-fortimicin B in 180 ml of 0.2 N hydrochloric acid in methanol is hydrogenolyzed over 1.2 g of 5% palladium on carbon for 4 hours. The catalyst is removed by filtration through a celite mat. The filtrate is concentrated to dryness under reduced pressure and excess hydrochloric acid is removed by repeated co-distillation with methanol under reduced pressure to give the desired product.

EXAMPLE 30

2-N-Acetyl-6'-epi-fortimicin B

An aqueous solution of 0.840 g. of 4-N-acetyl-6'-epi-fortimicin B trihydrochloride is passed through a column (1.1×19 cm) of an anion exchange resin, quaternary ammonium sytrene type, e.g., Bio-Rad Laboratories' AG ® 2-X8, 50–100 mesh,(hydroxy form), sufficient to remove the chloride ion. The basic elutes are collected and diluted to 84 ml with water. After standing at room temperature for 20 days the solution is evaporated under reduced pressure to a small volume and chromatographed on a column of a cation exchange resin, carboxylic type, e.g., Bio-Rad Laboratories' Bio-Rex 70, 100–200 mesh, (ammonium form). Elution with a gradient of water to 1 N ammonium hydroxide gives fractions containing only 2'-N-acetyl-6'-epi-fortimicin B. These fractions are concentrated to dryness under reduced pressure to give the desired product.

EXAMPLE 31

1,6'-Di-N-benzyloxycarbonyl-2'-N-acetyl-6'-epi-fortimicin B

A stirred solution of 0.290 g. of 2'-N-acetyl-6'-epi-fortimicin B in 4.5 ml of water and 9.0 ml of methanol, cooled to 0° in an ice bath, is treated with 0.388 g of N-(benzyloxycarbonyloxy)succinimide. Stirring is continued at 0° for 3 hours and then at room temperature for 22 hours. The solution is concentrated under reduced pressure to an oil which is shaken with a mixture of 100 ml of chloroform and 75 ml of water. The chloroform layer is separated and the aqueous portion is shaken with an additional 100 ml of chloroform. The combined chloroform solutions are washed two times with water and dried over anhydrous magnesium sulfate. Evaporation of the chloroform under reduced pressure leaves 0.480 g of colorless solid. The solid is chromatographed on a column (2.0×43 cm) of silica gel prepared and eluted with a solvent system consisting of chloroform, methanol-concentrated ammonium hydroxide (23.4:1.4:01 v/v/v) to give the desired product.

EXAMPLE 32

Tri-N-benzyloxycarbonyl-2'-N-acetyl-6'-epi-fortimicin A

To a stirred solution of 0.150 g of 1,6'-di-N-benzyloxycarbonyl-2'-N-acetyl-6'-epi-fortimicin B, 0.065 g of N-benzyloxycarbonylglycine and 0.074 g of 1-hydroxybenzotriazole monohydrate in 2.0 ml of tetrahydrofuran is added a solution of 0.069 g of N,N'-dicyclohexylcarbodiimide in 2.0 ml of tetrahydrofuran. Stirring is continued at room temperature for 23 hours. The precipitated N,N'-dicyclohexylurea is removed by filtration. The filtrate is evaporated under reduced pressure to leave 0.299 g of product. The product is chromatographed on a column of silica gel, prepared and eluted with a solvent system consisting of benzene-methanol-95% ethanol-ammonium hydroxide (23.5:1.4:2.0:0.2 v/v). Fractions containing the desired product were taken to dryness under reduced pressure leaving the desired product.

EXAMPLE 33

2'-N-Acetyl-6'-epi-fortimicin A Trihydrochloride

A solution of 0.178 g of tri-N-benzyloxycarbonyl-2'-N-acetyl-6'-epi-fortimicin A in 30 ml of 0.2 N hydrochloric acid in methanol is hydrogenolyzed for 4 hours under 3 atmospheres of hydrogen in the presence of 0.178 g of 5% palladium on carbon. The catalyst is removed by filtration through a celite mat. The filtrate is concentrated to a small volume and treated with activated carbon, e.g., Darco ® G-60, Atlas Chemical Industries, Inc. The carbon is removed by filtration through a celite mat. The filtrate is concentrated to dryness and excess hydrochloric acid is removed by repeated co-distillation with methanol under reduced pressure to give the desired product.

EXAMPLE 34

2'-N-(β-Aminoethyl)-6'-epi-fortimicin B

A stirring solution of 2.0 g of 2'-N-glycyl-6'-epi-fortimicin B in 80 ml of tetrahydrofuran is treated with 1.22 g of lithium aluminum hydride. The stirring reaction mixture is refluxed for 20 hours and then the excess lithium aluminum hydride is consumed by the careful addition of water. The insoluble material is sedimented by centrifugation. The pellet is suspended in 50 ml of water and centrifuged. The combined supernatants are taken to dryness under reduced pressure to give 1.44 g of brown solid. The solid is chromatographed on a column (2.0×40 cm) of cation exchange resin, carboxylic type, e.g., Bio-Rad Laboratories, Bio-Rex 70, 100–200 mesh, ammonia form, and eluted with a gradient of water to 1 N ammonium hydroxide. Fractions containing the desired product are concentrated to a small volumne and lyophilized to give the desired product.

EXAMPLE 35

1,6'-Di-N-benzyloxycarbonyl-2'-N-[N-benzyloxycarbonyl(β-aminoethyl)]-6'-epi-fortimicin B A stirred solution of 0.824 g of 2'-N-(β-aminoethyl)-6'-epi-fortimicin B in 12.4 ml of water and 24.8 ml of methanol cooled to 4° in an ice bath, is treated with 1.83 g of N-(benzyloxycarbonyloxy)succinimide. Stirring is continued at 4° for 3 hours and then at room temperature for 22 hours. The reaction mixture is concentrated to an oil under reduced pressure and then it is shaken with a mixture of 150 ml of chloroform and 75 ml of water. The chloroform layer is separated and washed with 75 ml of water. The aqueous portions are then washed in series with two 80 ml portions of chloroform. The combined chloroform solution is dried over anhydrous magnesium sulfate and concentrated to dryness under reduced pressure to give 1.584 g of colorless solid. The solid is chromatographed on a column (2.2×65 cm) of silica gel prepared and eluted with a solvent system consisting of benzene-methanol-95% ethanol-concentrated ammonium hydroxide (23.5:1.4:2.0:0.2 v/v/v/v) to the desired product.

EXAMPLE 36

1,6'-Di-N-benzyloxycarbonyl-4-N-(N-benzyloxycarbonylglycyl)-2'-N-[N-benzyloxycarbonyl-(β-aminoethyl)]-6'-epi-fortimicin B A stirred solution of 0.503 g of tri-N-benzyloxycarbonyl-2'-N-[N-benzyloxycarbonyl(β-aminoethyl)]-6'-epi-fortimicin B in 3.4 ml of tetrahydrofuran is treated with 0.223 g of the N-hydroxysuccinimide ester of N-benzyloxycarbonylglycine. After stirring for 20 hours at room temperature the tetrahydrofuran is evaporated under reduced pressure to leave 0.714 g of colorless solid. The solid is chromatographed on a column (1.5×74 cm) of silica gel eluted with a solvent system consisting of benzene-methanol-95% ethanol-concentrated ammonium hydroxide (23.5:1.4:2.0:0.2 v/v/v/v) to give the desired product.

EXAMPLE 37

2'-N-(β-Aminoethyl)-6'-epi-fortimicin A Pentahydrochloride

A solution of 0.426 g of 1,6'-di-N-benzyloxycarbonyl-4-N-(N-benzyloxycarbonylglycyl-2'-N-[N-benzyloxycarbonyl(β-aminoethyl)]-6'-epi-fortimicin B in 70 ml of 0.2 N methanolic hydrochloric acid is hydrogenolyzed over 0.40 g of 5% palladium on carbon for 4 hours. The catalyst, collected by filtration through a celite mat, is washed with several small portions of methanol. The filtrate is evaporated to dryness under reduced pressure. Excess hydrochloric acid is removed by repeated co-distillation with methanol under reduced pressure to give 2'-N-(β-aminoethyl)-6'-epi-fortimicin A pentahydrochloride.

The compounds of this invention are active as systemic antibiotics when injected by parenteral routes of administration, i.e., by the intramuscular, intravenous, intraperitoneal or subcutaneous routes of administration. The compounds can also be administered orally in those instances where it is desirable to sterilize the intestional tract and can additionally be applied topically or rectally.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides, such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized, by for example, filtration through a bacteria-retaining filter, by incorporating sterilizing agents into the compositions. They can also be manufactured in the form of sterile solid compositions which can be dissolved in sterile water, or some other sterile injectable medium immediately before use.

Compositions for rectal administration are preferably suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 1 to 200 mg/kg of body weight daily are administered to a mammalian patient suffering from an infection caused by susceptible organism.

The antibacterial activity of the compounds of this invention is initially determined by a two-fold dilution test using Meuller-Hinton agar, 10 ml per Petri plate. The inoculum of approximately $1 \times 10^5$ of the indicated test organism is delivered by the Steer's replicator. The test is incubated at 37° C. for 24 hours.

We claim:

1. 2'-N-substituted, 6'-epi fortimicins B represented by the formula:

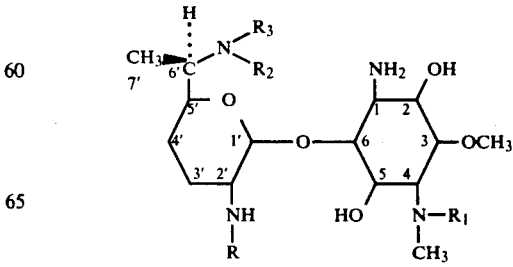

wherein: R is acyl, hydroxyacyl, aminoacyl, N-monoloweralkylaminoacyl, N,N-diloweralkylaminoacyl, hydroxy-substituted aminoacyl, an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, or N,N-diloweralkylaminohydroxyloweralkyl; and $R_1$ is acyl, aminoacyl, N-monoloweralkylaminoacyl, N,N-diloweralkylaminoacyl, hydroxy-substituted aminoacyl, an amino acid residue, loweralkyl, aminoloweralkyl, hydroxyloweralkyl, N-loweralkylaminoloweralkyl, hydroxyacyl, N,N-diloweralkylaminoloweralkyl, aminohydroxyloweralkyl, N-loweralkylaminohydroxyloweralkyl, N,N-diloweralkylaminohydroxyloweralkyl or hydrogen $R_2$ is lower alkyl; $R_3$ is hydrogen or lower alkyl and wherein acyl is represented by the formula

wherein Y is loweralkyl; and the pharmaceutically acceptable salts thereof.

2. A compound of claim 1 wherein $R_1$ is hydrogen.

3. A compound of claim 2: 2'-N-glycyl-6'-epi-fortimicin B or a pharmaceutically acceptable salt thereof.

4. A compound of claim 2: 2'-N-acetyl-6'-epi-fortimicin B or a pharmaceutically acceptable salt thereof.

5. A compound of claim 2: 2'-N-($\beta$-aminoethyl)-6'-epi-fortimicin B or a pharmaceutically acceptable salt thereof.

6. A compound of claim 1 wherein both R and $R_1$ are an amino acid residue.

7. A compound of claim 6: 2'-N-glycyl-6'-epi-fortimicin A or a pharmaceutically acceptable salt thereof.

8. A compound of claim 1 wherein R is aminoloweralkyl.

9. A compound of claim 1 wherein R is an amino acid residue.

10. A pharmaceutical composition comprising a compound of claim 1 and a pharmaceutically acceptable carrier or diluent.

* * * * *